US005639858A

United States Patent [19]

Hoey et al.

[11] Patent Number: 5,639,858

[45] Date of Patent: Jun. 17, 1997

[54] HUMAN SIGNAL TRANSDUCER AND BINDING ASSAYS

[75] Inventors: Timothy Hoey, Woodside; Mike Rothe, So. San Francisco, both of Calif.

[73] Assignee: Tularik, Inc., South San Francisco, Calif.

[21] Appl. No.: 408,318

[22] Filed: Mar. 22, 1995

[51] Int. Cl.$^6$ .............................. A61K 38/16; C07K 14/00
[52] U.S. Cl. .......................... 530/350; 530/351; 530/331; 530/330; 530/329; 530/328; 530/327; 530/326; 530/325; 530/324
[58] Field of Search ..................................... 530/350, 351, 530/331, 330, 329, 328, 327, 326, 325, 324

[56] References Cited

PUBLICATIONS

Chua et al. (1994) J. Immunol. 153, 128–136.
Yamamoto et al. (1994) Mol and Cell Biol. 14:4342–4349.
Zhong et al. (1994) 91:4806–4810.
Yamamoto et al., "Stat4, a Novel Gamma Interferon Activation Site–Binding Protein Expressed in Early Myeloid Differention", Mol. and Cell Biol., vol. 14, pp. 4342–4349. 1994.

Primary Examiner—Cecilia J. Tsang
Assistant Examiner—Anish Gupta
Attorney, Agent, or Firm—Richard Aron Osman

[57] ABSTRACT

The invention provides methods and compositions relating to interleukin 12 signal transducers, particularly an isolated human signal transducer and activator of transcription 4 (hStat 4), or a fragment thereof having an hStat 4-specific binding affinity, nucleic acids encoding hStat 4, which nucleic acids may be part of hStat 4-expression vectors and may be incorporated into a recombinant cell, agents which selectively bind hStat 4 or hStat 4 intracellular binding targets, or disrupt the binding of hStat 4 to such intracellular targets, methods of making such agents and hStat 4-specific binding targets in the form of cell surface proteins and nucleic acids. An hStat 4 drug screening assay involves forming mixtures of an hStat 4, an intracellular hStat 4 binding target, and a prospective agent at different concentrations. The mixtures are incubated to permit the binding of the intracellular hStat 4 binding target to the hStat 4 and the mixtures are then analyzed for the presence of such binding. A difference in such binding between the first and second mixtures indicates that the agent is capable of modulating the binding of hStat 4 to an intracellular hStat 4 binding target.

40 Claims, No Drawings

HUMAN SIGNAL TRANSDUCER AND BINDING ASSAYS

FIELD OF THE INVENTION

The field of this invention is the human interleukin-12 signal transducter and activator of transcription.

BACKGROUND

Identifying and developing new pharmaceuticals is a multibillion dollar industry in the U.S. alone. Gene specific transcription factors provide a promising class of targets for novel therapeutics directed to these and other human diseases. Urgently needed are efficient methods of identifying pharmacological agents or drugs which are active at the level of gene transcription. Methods amenable to automated, cost-effective, high throughput drug screening have immediate application in a broad range of domestic and international pharmaceutical and biotechnology drug development programs. Interleukin-12 (IL-12) is an immunomodulatory cytokine secreted by macrophages, activated monocytes and B-cells. IL-12 is an important regulator of the effector phase of cell-mediated immunity, providing a crucial link in immune system surveillance for cellular infection, transformation, etc. For example, IL-12 is the most potent NK cell stimulator known, IL-12 stimulates the differentiation of naive CD4+T cells to the TH1 subset, and stimulates the differentiation of CD8+T cells into mature, functionally active CTLs.

As such, IL-12 signal transduction provides an important target for pharmaceutical intervention in the immune system, especially autoimmunity. Accordingly, it is desired to identify agents which specifically interfere with transduction of IL-12 signalling. Unfortunately, the reagents necessary for the development of high-throughput screening assays for such therapeutics are unavailable.

Relevant Literature

A subunit of the IL-12 receptor is described in Chua et al. (1994) J. Immunol 153, 128–136. Yamamoto et al (1994) Mol and Cell Biol 14:4342–4349 and Zhong et at. (1994) 91:4806–4810 disclose a mouse protein, reStat 4, with sequence similarity to hStat 4.

SUMMARY OF THE INVENTION

The invention provides methods and compositions relating to interleukin-12 signal transducers. In one embodiment, the invention provides isolated human signal transducer and activator of transcription 4 (hStat 4), or a fragment thereof having an hStat 4-specific binding affinity. The invention provides nucleic acids encoding the subject hStat 4 and hStat 4 fragments, which nucleic acids may be part of hStat 4-expression vectors and may be incorporated into a recombinant cell. The invention provides agents which selectively bind hStat 4 or hStat 4 intracellular binding targets, or disrupt the binding of hStat 4 to such intracellular targets, and methods of making such agents. The invention also provides specific hStat 4 binding targets in the form of cell surface proteins and nucleic acids.

The subject hStat 4 and hStat 4 fragments and find particular use in screening assays for agents or lead compounds for agents useful in the diagnosis, prognosis or treatment of disease, particularly disease associated with undesirable cell growth, differentiation and/or cytokine signal responsiveness. One such assay involves forming mixtures of an hStat 4, an intracellular hStat 4 binding target, and a prospective agent at different concentrations. Typically, one mixture is a negative control (i.e. the agent concentration is zero). The mixtures are incubated to permit the binding of the intracellular hStat 4 binding target to the hStat 4 and the mixtures are then analyzed for the presence of such binding. A difference in such binding between the first and second mixtures indicates that the agent is capable of modulating the binding of hStat 4 to an intracellular hStat 4 binding target.

DETAILED DESCRIPTION OF THE INVENTION

The invention provides methods and compositions relating to human interleukin-12 signal transducers including hStat 4. A cDNA encoding hStat 4 and its translation product are shown in SEQUENCE ID NOS: 1 and 2, respectively.

The subject hStat 4 fragments have one or more hStat 4-specific binding affinities which distinguish other Stats, including the ability to specifically bind at least one natural human intracellular hStat 4-specific binding target or a hStat 4-specific binding agent such as a hStat 4-specific antibody or a hStat 4-specific binding agent identified in assays such as described below. Accordingly, the specificity of hStat 4 fragment specific binding agents is confirmed by ensuring non-crossreactivity with other Stats including murine stat 4. Furthermore, preferred hStat 4 fragments are capable of eliciting an antibody capable of distinguishing hStat 4 from other Stats and reStat 4. Methods for making immunogenic peptides through the use of conjugates, adjuvants, etc. and methods for eliciting antibodies, e.g. immunizing rabbits, are well known.

Exemplary natural intracellular binding targets include nucleic acids which comprise one or more hStat 4 DNA binding sites such as the interleukin response element of the gene encoding FcγγRI, cell surface proteins such as the hStat 4 binding domain the IL-12 receptor and phosphotryrosine peptide fragments thereof, protein kinases such as Janus tyrosine kinases, transcription factors such as those comprising the transcription initiation complex, etc., and fragments of such targets which are capable of hStat 4-specific binding. Other natural hStat 4 binding targets are readily identified by screening cells, membranes and cellular extracts and fractions with the disclosed materials and methods and by other methods known in the art. For example, two-hybrid screening using hStat 4 fragments are used to identify intracellular targets which specifically bind such fragments. Preferred hStat 4 fragments retain the ability to specifically bind at least one of an hStat 4 DNA binding site and an intracellular domain of an IL-12 receptor subunit. For example, using a strategy analogous to that described in Hou et al. (1994) Science 265: 1701–1706, carboxyl terminus IL-12 receptor phosphotyrosine peptides are shown to inhibit hStat 4 DNA binding. IL-12 receptor variants lacking these two peptides are found to lose the ability to activate Star proteins. Convenient ways to verify the ability of a given hStat 4 fragment to specifically bind such targets include in vitro labelled binding assays such as described below, and EMSAs.

A wide variety of molecular and biochemical methods are available for generating and expressing hStat 4 fragments, see e.g. Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, N.Y., New York, 1992) or that are otherwise known in the art. For example, hStat 4 or fragments thereof may be obtained by chemical synthesis, expression in bacteria such as *E. coli* and eukaryotes such as yeast or vaccinia or baculovirus-based expression systems, etc., depending on the size, nature and quantity of the hStat 4 or fragment. The subject hStat 4 fragments are of length sufficient to provide a novel peptide. As used herein, such peptides are at least 5, usually at least about 6, more usually at least about 8, most usually at least about 10 amino acids. hStat 4 fragments may be present in a free state or bound to other components such as blocking groups to chemically insulate reactive groups (e.g. amines, carboxyls, etc.) of the peptide, fusion peptides or polypeptides (i.e. the peptide may be present as a portion of a larger polypeptide), etc.

The subject hStat 4 fragments maintain binding affinity of not less than six, preferably not less than four, more preferably not less than two orders of magnitude less than the binding equilibrium constant of a full-length native hStat 4 to the binding target under similar conditions. Particular hStat 4 fragments or deletion mutants are shown to function in a dominant-negative fashion. HStat 4 fragments containing tyrosine residue 693 is also shown to prevent tyrosine phosphorylation of hStat 4 thereby inhibiting hStat 4 activity. Such fragments provide therapeutic agents, e.g. when delivered by intracellular immunization-transfection of susceptible cells with nucleic acids encoding such mutants.

The claimed hStat 4 and hStat 4 fragments are isolated, partially pure or pure and are typically recombinantly produced. As used herein, an "isolated" peptide is unaccompanied by at least some of the material with which it is associated in its natural state and constitutes at least about 0.5%, preferably at least about 2%, and more preferably at least about 5% by weight of the total protein (including peptide) in a given sample; a partially pure peptide constitutes at least about 10%, preferably at least about 30%, and more preferably at least about 60% by weight of the total protein in a given sample; and a pure peptide constitutes at least about 70%, preferably at least about 90%, and more preferably at least about 95% by weight of the total protein in a given sample.

The invention provides hStat 4-specific binding agents, methods of identifying and making such agents, and their use in diagnosis, therapy and pharmaceutical development. For example, hStat 4-specific agents are useful in a variety of diagnostic applications, especially where disease or disease prognosis is associated with immune disfunction resulting from improper expression of hStat 4. Novel hStat 4-specific binding agents include hStat 4-specific antibodies; novel nucleic acids with sequence similarity to that of the FcγRI receptor promoter as described below; isolated IL-12 receptor subunit domains; other natural intracellular binding agents identified with assays such as one- and two-hybrid screens; non-natural intracellular binding agents identified in screens of chemical libraries, etc.

Generally, hStat 4-specificity of the binding target is shown by binding equilibrium constants. Such targets are capable of selectively binding a hStat 4, i.e. with an equilibrium constant at least about $10^7 M^{-1}$, preferably at least about $10^8 M^{-1}$, more preferably at least about $10^9 M^{-1}$. A wide variety of cell-based and cell-free assays may be used to demonstrate hStat 4-specific binding. Cell based assays include one and two-hybrid screens, mediating or competitively inhibiting hStat 4-mediated transcription, etc. Preferred are rapid in vitro, cell-free assays such as mediating or inhibiting hStat 4-protein (e.g. hStat 4-IL-12 receptor subunit binding), hStat 4-nucleic acid binding, immunoassays, etc. Other useful screening assays for hStat 4/hStat 4 fragment-target binding include fluorescence resonance energy transfer (FRET), electrophoretic mobility shift analysis (EMSA), etc.

The invention also provides nucleic acids encoding the subject hStat 4 and hStat 4 fragments, which nucleic acids may be part of hStat 4-expression vectors and may be incorporated into recombinant cells for expression and screening, transgenic animals for functional studies (e.g. the efficacy of candidate drugs for disease associated with expression of a hStat 4), etc. In addition, the invention provides nucleic acids sharing substantial sequence similarity with that of one or more wild-type hStat 4 nucleic acids. Substantially identical or homologous nucleic acid sequences hybridize to their respective complements under high stringency conditions, for example, at 55° C. and hybridization buffer comprising 50% formamide in 0.9M saline/0.09M sodium citrate (SSC) buffer and remain bound when subject to washing at 55° C. with the SSC/formamide buffer. Where the sequences diverge, the differences are preferably silent, i.e. or a nucleotide change providing a redundant codon, or conservative, i.e. a nucleotide change providing a conservative amino acid substitution.

The subject nucleic acids find a wide variety of applications including use as hybridization probes, PCR primers, therapeutic nucleic acids, etc. for use in detecting the presence of hStat 4 genes and gene transcripts, for detecting or amplifying nucleic acids with substantial sequence similarity such as hStat 4 homologs and structural analogs, and for gene therapy applications. Given the subject probes, materials and methods for probing cDNA and genetic libraries and recovering homologs are known in the art. Preferred libraries are derived from human immune cells, especially cDNA libraries from differentiated and activated human lymphoid cells. In one application, the subject nucleic acids find use as hybridization probes for identifying hStat 4 cDNA homologs with substantial sequence similarity. These homologs in turn provide additional Stats and Stat fragment for use in binding assays and therapy as described herein. hStat 4 encoding nucleic acids also find applications in gene therapy. For example, nucleic acids encoding dominant-negative hStat 4 mutants are cloned into a virus and the virus used to transfect and confer disease (e.g. autoimmune disease) resistance to the transfected cells.

Therapeutic hStat 4 nucleic acids are used to modulate, usually reduce, cellular expression or intracellular concentration or availability of active hStat 4. These nucleic acids are typically antisense: single-stranded sequences comprising complements of the disclosed hStat 4 nucleic acids. Antisense modulation of hStat 4 expression may employ hStat 4 antisense nucleic acids operably linked to gene regulatory sequences. Cell are transfected with a vector comprising an hStat 4 sequence with a promoter sequence oriented such that transcription of the gene yields an antisense transcript capable of binding to endogenous hStat 4 encoding mRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a hStat 4 or hStat 4 fragment may be administered to the target cell, in or temporarily isolated from a host, at a concentration that results in a substantial reduction in hStat 4 expression. For gene therapy involving the transfusion of hStat 4 transfected cells, administration will depend on a number of variables that are ascertained empirically. For example, the number of cells will vary depending on the stability of the transfused cells. Transfusion media is typically a buffered saline solution or other pharmacologically acceptable solution. Similarly the amount of other administered compositions, e.g. transfected nucleic acid, protein, etc., will depend on the manner of administration, purpose of the therapy, and the like.

The subject nucleic acids are often recombinant, meaning they comprise a sequence joined to a nucleotide other than that which it is joined to on a natural chromosome. An isolated nucleic acid constitutes at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction.

The invention provides efficient methods of identifying pharmacological agents or drugs which are active at the level of hStat 4 modulatable cellular function, particularly hStat 4 mediated interleukin signal transduction. Generally, these screening methods involve assaying for compounds which interfere with hStat 4 activity such as hStat 4-IL-12 receptor binding, hStat 4-DNA binding, etc. The methods are amenable to automated, cost-effective high throughput drug screening and have immediate application in a broad range of domestic and international pharmaceutical and biotechnology drug development programs.

Target therapeutic indications are limited only in that the target cellular function (e.g. gene expression) be subject to modulation, usually inhibition, by disruption of the formation of a complex (e.g. transcription complex) comprising a hStat 4 or hStat 4 fragment and one or more natural hStat 4 intracellular binding targets. Since a wide variety of genes are subject to hStat 4 regulated gene transcription, target indications may include viral, bacterial and fungal infections, metabolic disease, genetic disease, cell growth and regulatory disfunction, such as neoplasia, inflammation, hypersensitivity, etc. Frequently, the target indication is related to either immune dysfunction or selective immune suppression.

A wide variety of assays for binding agents are provided including labelled in vitro protein-protein and protein-DNA binding assay, electrophoretic mobility shift assays, immunoassays for protein binding or transcription complex formation, cell based assays such as one, two and three hybrid screens, expression assays such as transcription assays, etc. For example, three-hybrid screens are used to rapidly examine the effect of transfected nucleic acids, which may, for example, encode combinatorial peptide libraries or antisense molecules, on the intracellular binding of hStat 4 or hStat 4 fragments to intracellular hStat 4 targets. Convenient reagents for such assays (e.g. GAL4 fusion partners) are known in the art.

hStat 4 or hStat 4 fragments used in the methods are usually added in an isolated, partially pure or pure form and are typically recombinantly produced. The hStat 4 or fragment may be part of a fusion product with another peptide or polypeptide, e.g. a polypeptide that is capable of providing or enhancing protein-protein binding, sequence-specific nucleic acid binding or stability under assay conditions (e.g. a tag for detection or anchoring).

The assay mixtures comprise at least a portion of a natural intracellular hStat 4 binding target such as an IL-12 receptor subunit domain or a nucleic acid comprising a sequence which shares sufficient sequence similarity with a gene or gene regulatory region to which the native hStat 4 naturally binds to provide sequence-specific binding of the hStat 4 or hStat 4 fragment. Such a nucleic acid may further comprise one or more sequences which facilitate the binding of a second transcription factor or fragment thereof which cooperatively binds the nucleic acid with the hStat 4 (i.e. at least one increases the affinity or specificity of the DNA binding of the other). While native binding targets may be used, it is frequently preferred to use portions (e.g. peptides, nucleic acid fragments) or analogs (i.e. agents which mimic the hStat 4 binding properties of the natural binding target for the purposes of the assay) thereof so long as the portion provides binding affinity and avidity to the hStat 4 conveniently measurable in the assay. Binding sequences for other transcription factors may be found in sources such as the Transcription Factor Database of the National Center for Biotechnology Information at the National Library for Medicine, in Faisst and Meyer (1991) Nucleic Acids Research 20, 3–26, and others known to those skilled in this art. In addition, other high affinity natural and non-natural DNA binding sites may be generated by known methods, e.g. Blackwell and Weintraub (1990) Science 25: 1104–1110.

The hStat 4 fragment is selected to provide specific binding to the selected intracellular binding target. For example, where the target is the IL-12 receptor or receptor portion, the hStat 4 fragment will generally include the SH2 domain (residues 569–668).

Where used, the nucleic acid portion bound by the peptide (s) may be continuous or segmented and is usually linear and double-stranded DNA, though circular plasmids or other nucleic acids or structural analogs may be substituted so long as hStat 4 sequence-specific binding is retained. In some applications, supercoiled DNA provides optimal sequence-specific binding and is preferred. The nucleic acid may be of any length amenable to the assay conditions and requirements. Typically the nucleic acid is between 8 bp and 5 kb, preferably between about 12 bp and 1 kb, more preferably between about 18 bp and 250 bp, most preferably between about 27 and 50 bp. Additional nucleotides may be used to provide structure which enhances or decreased binding or stability, etc. For example, combinatorial DNA binding can be effected by including two or more DNA binding sites for different or the same transcription factor on the oligonucleotide. This allows for the study of cooperative or synergistic DNA binding of two or more factors. In addition, the nucleic acid can comprise a cassette into which transcription factor binding sites are conveniently spliced for use in the subject assays.

The assay mixture also comprises a candidate pharmacological agent. Generally a plurality of assay mixtures are run in parallel with different agent concentrations to obtain a differential response to the various concentrations. Typically, one of these concentrations serves as a negative control, i.e. at zero concentration or below the limits of assay detection. Candidate agents encompass numerous chemical classes, though typically they are organic compounds; preferably small organic compounds. Small organic compounds have a molecular weight of more than 50 yet less than about 2,500, preferably less than about 1000, more preferably, less than about 500. Candidate agents comprise functional chemical groups necessary for structural interactions with proteins and/or DNA, and typically include at least an amine, carbonyl, hydroxyl or carboxyl group, preferably at least two of the functional chemical groups, more preferably at least three. The candidate agents often comprise cyclical carbon or heterocyclic structures and/or aromatic or polyaromatic structures substituted with one or more of the forementioned functional groups. Candidate agents are also found among biomolecules including peptides, saccharides, fatty acids, steroids, purines, pyrimidines, derivatives, structural analogs or combinations thereof, and the like. Where the agent is or is encoded by a transfected nucleic acid, said nucleic acid is typically DNA or RNA.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc., to produce structural analogs.

A variety of other reagents may also be included in the mixture. These include reagents like salts, buffers, neutral proteins, e.g. albumin, detergents, etc. which may be used to facilitate optimal protein-protein and/or protein-nucleic acid binding and/or reduce non-specific or background interactions, etc. Also, reagents that otherwise improve the efficiency of the assay, such as protease inhibitors, nuclease inhibitors, antimicrobial agents, etc. May be used.

The resultant mixture is incubated under conditions whereby, but for the presence of the candidate pharmacological agent, the hStat 4 specifically binds the cellular binding target, portion or analog. The mixture components can be added in any order that provides for the requisite bindings. Incubations may be performed at any temperature which facilitates optimal binding, typically between 4 and 40° C., more commonly between 15 and 40° C. Incubation periods are likewise selected for optimal binding but also minimized to facilitate rapid, high-throughput screening, and are typically between 0.1 and 10 hours, preferably less than 5 hours, more preferably less than 2 hours.

After incubation, the presence or absence of specific binding between the hStat 4 and one or more binding targets is detected by any convenient way. For cell-free binding type assays, a separation step is often used to separate bound from unbound components. The separation step may be accomplished in a variety of ways. Conveniently, at least one of the components is immobilized on a solid substrate which may be any solid from which the unbound components may be conveniently separated. The solid substrate may be made of a wide variety of materials and in a wide variety of shapes, e.g. microtiter plate, microbead, dipstick, resin particle, etc. The substrate is chosen to maximize signal to noise ratios, primarily to minimize background binding, for ease of washing and cost.

Separation may be effected for example, by removing a bead or dipstick from a reservoir, emptying or diluting reservoir such as a microtiter plate well, rinsing a bead (e.g. beads with iron cores may be readily isolated and washed using magnets), particle, chromatographic column or filter with a wash solution or solvent. Typically, the separation step will include an extended rinse or wash or a plurality of rinses or washes. For example, where the solid substrate is a microtiter plate, the wells may be washed several times with a washing solution, which typically includes those components of the incubation mixture that do not participate in specific binding such as salts, buffer, detergent, nonspecific protein, etc. may exploit a polypeptide specific binding reagent such as an antibody or receptor specific to a ligand of the polypeptide.

Detection may be effected in any convenient way. For cell based assays such as one, two, and three hybrid screens, the transcript resulting from hStat 4-target binding usually encodes a directly or indirectly detectable product (e.g. galactosidase activity, luciferase activity, etc.). For cell-free binding assays, one of the components usually comprises or is coupled to a label. A wide variety of labels may be employed—essentially any label that provides for detection of bound protein. The label may provide for direct detection as radioactivity, luminescence, optical or electron density, etc. or indirect detection such as an epitope tag, an enzyme, etc. The label may be appended to the protein e.g. a phosphate group comprising a radioactive isotope of phosphorous, or incorporated into the protein structure, e.g. a methionine residue comprising a radioactive isotope of sulfur.

A variety of methods may be used to detect the label depending on the nature of the label and other assay components. For example, the label may be detected bound to the solid substrate or a portion of the bound complex containing the label may be separated from the solid substrate, and thereafter the label detected. Labels may be directly detected through optical or electron density, radiative emissions, nonradiative energy transfers, etc. or indirectly detected with antibody conjugates, etc. For example, in the case of radioactive labels, emissions may be detected directly, e.g. with particle counters or indirectly, e.g. with scintillation cocktails and counters. The methods are particularly suited to automated high throughput drug screening. Candidate agents shown to inhibit hStat 4-target binding or transcription complex formation provide valuable reagents to the pharmaceutical industries for animal and human trials.

As previously described, the methods are particularly suited to automated high throughput drug screening. In a particular embodiment, the arm retrieves and transfers a microtiter plate to a liquid dispensing station where measured aliquots of each an incubation buffer and a solution comprising one or more candidate agents are deposited into each designated well. The arm then retrieves and transfers to and deposits in designated wells a measured aliquot of a solution comprising a labeled transcription factor protein. After a first incubation period, the liquid dispensing station deposits in each designated well a measured aliquot of a biotinylated nucleic acid solution. The first and/or following second incubation may optionally occur after the arm transfers the plate to a shaker station. After a second incubation period, the arm transfers the microtiter plate to a wash station where the unbound contents of each well is aspirated and then the well repeatedly filled with a wash buffer and aspirated. Where the bound label is radioactive phosphorous, the arm retrieves and transfers the plate to the liquid dispensing station where a measured aliquot of a scintillation cocktail is deposited in each designated well. Thereafter, the amount of label retained in each designated well is quantified.

In more preferred embodiments, the liquid dispensing station and arm are capable of depositing aliquots in at least eight wells simultaneously and the wash station is capable of filling and aspirating ninety-six wells simultaneously. Preferred robots are capable of processing at least 640 and preferably at least about 1,280 candidate agents every 24 hours, e.g. in microtiter plates. Of course, useful agents are identified with a range of other assays (e.g. gel shifts, etc.) employing the subject hStat 4 and hStat 4 fragments.

The subject hStat 4 and hStat 4 fragments and nucleic acids provide a wide variety of uses in addition to the in vitro binding assays described above. For example, cell-based assays are provided which involve transfecting an IL-12 receptor subunit or functional fragment thereof expressing cell with an hStat 4 inducible reporter such as luciferase. Agents which modulate hStat 4 mediated cell function are then detected through a change in the reporter. Another approach is a transient expression assay. In this method, cells are transfected with one or more constructs encoding in sum, a polypeptide comprising a portion of hStat 4 capable of selectively binding an natural IL-12 receptor target and a reporter under the transcriptional control of a promoter comprising a functional hStat 4 binding site. The cell may advantageously also be cotransfected with a construct encoding an hStat 4 activator, usually a tyrosine kinase, particularly a Jak kinase.

The subject compositions also provide therapeutic applications. For example, hStat 4 peptides comprising IL-12 receptor, DNA or transcription factor interaction domains or IL-12 receptor peptides capable of selectively binding said hStat 4 peptides find use in treating disease associated with undesirable cell growth, differentiation, particularly immune cell differentiation, and cytokine, particularly interleukin, more particularly IL-12, responsiveness. For therapeutic uses, the compositions and agents disclosed herein may be administered by any convenient way, preferably parenterally, conveniently in a physiologically acceptable carrier, e.g., phosphate buffered saline, saline, deionized water, or the like. Typically, the compositions are added to a retained physiological fluid such as blood or synovial fluid. Generally, the amount administered will be empirically determined, typically in the range of about 10 to 1000 µg/kg of the recipient. For peptide agents, the concentration of will generally be in the range of about 100 to 500 µg/ml in the dose administered. Other additives may be included, such as stabilizers, bactericides, etc. These additives will be present in conventional amounts.

The following examples are offered by way of illustration and not by way of limitation.

EXPERIMENTAL

Immunodepletion, supershifting and oligonucleotide competition assays:

Protein:DNA complexes were visualized by a gel mobility shift assay under non-denaturing conditions. Specificity of protein:DNA interaction was tested using 100-fold molar excess of either the native FcgRI probe (5'-GTATTTCCCAGAAAAGGAAC-3', SEQUENCE ID NO: 3) or the mutated derivative (5' -GTATCACCCAG TCAAGGAAC-3', SEQUENCE ID NO: 4). Antibody supershift experiments were performed by incubating protein samples with antibodies (Santa Cruz Biotech) for 30 minutes at 4° C. prior to exposure to the FcgRI DNA probe. Proteins purified from YT cells were purged of Stat 1, Stat 3 and Stat 4 by immunodepletion. 500 mg of each antibody (specific to Stat 1, Stat 3 and Stat 4) were incubated for 2 hours at room temperature with a slurry of protein-A Sepharose beads (Pharmacia) sufficient to yield 100 ml of bed volumn. Beads were washed three times with 1 ml of buffer C and then incubated for 2 hours at room temperature with Stat proteins purified from IL-12 induced YT cells. Beads were recovered by centrifugation and washed three times with 1 ml of buffer C. Unbound, wash and bound fractions were recovered and subjected to SDS-gel electrophoresis for subsequent staining with Coomassie blue, anti-phosphotyrosine antibodies and Star antibodies.

Cloning of hStat 4 cDNA:

In order to clone human STAT4 cDNAs, oligonucleotides were designed for PCR. The goal was to obtain a fragment that would specifically hybridize hSTAT4 yet none of the other members of the STAT family. Employing manual and computer-assisted sequence alignments of existing STAT cDNA, we attempted to identify regions combining high STAT divergence and low codon degeneracy for primer design, flanking a region optimized for effective library hybridization. The primer designs ultimately selected for use are indicated below. The degenerate positions are indicated by lower case letters separated by slashes.

MR15 =TTc/t CAc/t GGg/a/t/c AAc/t CCg/a/t/c ATG CA

MR16 =TT c/tTT g/aTC g/a/t/cCC TTG a/g TC CAT

MR17 =TC g/aTT g/a/t/c AC g/a/t/cAT t/cTG g/a/t/cGT CAT

MR15 corresponds to amino acids 94–100. MR16 is the reverse complement of amino acids 181–187. MR17 is the reverse complement of 216–222. Reverse transcriptase and polymerase chain reactions were carried out with polyA+ RNA from the human T cell line Jurkat as described below.

9.5 ml $H_2O$; 2.0 ml mRNA; 1.0 ml oligo dT primer 65° C. 12 min.; 22° C. 2 min.

1 ml RNAse inhibitor; 4 ml 5× RT buffer; 1 ml 100 mM dNTPs; 1 ml sodium; pyrophosphate; 0.5 ml Reverse Transcriptase 42° C. 60 min.; 95° C. 3 min.

50 ml Polymerase Chain Reactions were set up as follows:

29 ml $H_2O$; 5 ml 10× buffer (100 mM TRIS pH 8.3, 50 mM KCl); 3 ml 25 mM $MgCl_2$; 1.5 ml each primer; 1.5 ml DNA (from reverse transcription reaction); 1 ml Taq poymerase (diluted 1:4)

6 min 95° C.; 35 cycles of 95° C. 45 sec; 55° C. 1 min; 72° C. 3 min.

The combination of MR15 and MR16 yielded a product of the correct size of approximately 280 bp. This fragment was subcloned, sequenced, and confirmed to be derived from the human STAT4 gene. The combination of MR15 and MR17 could not successfully amplify human STAT4.

The portion of the human STAT4 gene that was obtained by PCR was used to screen a Jurkat cell library prepared in the following manner: Jurkat T cells were grown in RPMI +10% fetal bovine serum. Total RNA was isolated according to the Guanidinium-HCl method (Chomczynski and Sacchi, 1987. Anal. Biochem. 162, 156–159.). Poly-A+RNA was purified using oligo-dT magnetic beads (Promega). Random primed and oligo-dT primed libraries were prepared. The cDNA libraries were constructed in the vector Lambda ZAPII (Stratagene) according to the protocol supplied by the manufacturer. The cDNA was size selected for greater than 1 kb by electrophoresis a on 5% polyacrylamide gel prior to ligation. Each library contained approximately $2 \times 10_6$ recombinant clones.

The STAT4 PCR fragment was labeled by random priming and hybridized in 1M NaCl, 50 mM Tris pH 7.4, 2 mM EDTA, 10×Denhardt's, 0.05% SDS, and 50 mg/ml salmon sperm DNA at 65° C. The filters were washed first in 2×SSC, 0.1% SDS, and then in 0.2×SSC, 0.1% SDS at 65°C. Eight cross-hybridizing clones were identified after screening $1 \times 10^6$ recombinants. Hybridizing clones were purified and converted into Bluescript plasmid DNA clones. The three largest clones were chosen for sequence analysis. The DNA sequence was determined using thermal cycle sequencing and the Applied Biosystems 373A sequencer. These cDNAs were determined to be identical at their 3' ends and variable in length at the 5' ends. The sequence reported here is from the longest of the cDNA clones.

EXAMPLES

1. Protocol for hStat 4 - IL-12 Receptor-peptide binding assay.
   A. Reagents:
   Neutralite Avidin: 20 μg/ml in PBS.
   Blocking buffer: 5% BSA, 0.5% Tween 20 in PBS; 1 hr, RT.
   Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
   $^{33}$P hStat 4 10×stock: $10^{-8}$–$10^{-6}$M "cold" hStat 4 inactive (not tyr-phosporylated) and truncated (SH2 domain) hStat 4 supplemented with 200,000–250,000 cpm of labeled, inactive and truncated hStat 4 (Beckman counter). Place in the 4° C. microfridge during screening.
   Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.
   IL-12-receptor-peptides: $10^{-8}$ –$10^{-5}$M of each IL-12 receptor biotinylated peptides in PBS.
   B. Preparation of assay plates:
   Coat with 120 μl of stock N-Avidin per well overnight at 4° C.
   Wash 2× with 200 μl PBS.
   Block with 150 μl of blocking buffer.
   Wash 2× with 200 μl PBS.
   C. Assay:
   Add 40 μl assay buffer/well.
   Add 10 μl compound or extract.
   Add 10 μl $^{33}$P-hStat 4 (20,000–25,000 cpm/0.1–10 pmoles/well=$10^{-9}$–$10_{-7}$ M final concentration).
   Shake at 25° C. for 15 min.
   Incubate additional 45 min. at 25° C.
   Add 40 μl IL-12 receptor peptide mixture (0.1–10 pmoles/ 40 ul in assay buffer)
   Incubate 1 hr at RT.
   Stop the reaction by washing 4× with 200/ μl PBS.
   Add 150 μl scintillation cocktail.
   Count in Topcount.
   D. Controls for all assays (located on each plate):
   a. Non-specific binding (no receptor peptide added)
   b. Soluble (non-biotinylated receptor peptide) at 80% inhibition.

2. Protocol for hStat 4-DNA binding assay.
   A. Reagents:
   Neutralite Avidin: 20 μg/ml in PBS.
   Blocking buffer: 5% BSA, 0.5% Tween 20 in PBS; 1 hr, RT.
   Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
   $^x$P hStat 4 10×stock: $10^{-6}$–$10^{-8}$M "cold" hStat 4 supplemented with 200,000–250,000 cpm of labeled hStat 4 (Beckman counter). Place in the 4° C. microfridge during screening.
   Protease inhibitor cocktail (1000×): 10 mg Trypsin Inhibitor (BMB#109894), 10 mg Aprotinin (BMB #236624), 25 mg Benzamidine (Sigma #B-6506), 25 mg Leupeptin (BMB #1017128), 10 mg APMSF (BMB #917575), and 2 m NaVo$_3$ (Sigma #S-6508) in 10 ml of PBS.
   Oligonucleotide stock: (specific biotinylated). Biotinylated oligo at 17 pmole/μl, hStat 4 binding site: (BIOTIN) -GTATTTCCCAGAAAAGGAAC (SEQUENCE ID NO: 3)
   B. Preparation of assay plates:
   Coat with 120 μl of stock N-Avidin per well overnight at 4° C.
   Wash 2× with 200 μl PBS.
   Block with 150 μl of blocking buffer.
   Wash 2× with 200 μl PBS.
   C. Assay:
   Add 40 μl assay buffer/well.
   Add 10 μl compound or extract.
   Add 10 μl $^{33}$P-hStat 4 (20,000–25,000 cpm/0.1–10 pmoles/well=$10^{-9}$–$10^{-7}$M final concentration).
   Shake at 25° C. for 15 min.
   Incubate additional 45 min. at 25 C.
   Add 40 μl oligo mixture (1.0 pmoles/40 ul in assay buffer with 1 ng of ss-DNA)
   Incubate 1 hr at RT.
   Stop the reaction by washing 4× with 200 PBS.
   Add 150 μl scintillation cocktail.
   Count in Topcount.
   Controls for all assays (located on each plate):
   a. Non-specific binding (no oligo added)
   b. Specific soluble oligo at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated human signal transducer and activator of transcription 4 (hStat 4) protein comprising the amino acid sequence of SEQ ID NO:2 or a fragment thereof having an hStat 4-specific binding affinity, wherein the fragment of SEQ ID NO:2 comprises at least one of residue 40, 45, 123, 148, 184, 189, 190, 220, 221, 229, 232, 240, 274, 280, 295, 298, 300, 304, 332, 381, 387, 409, 411, 413, 443, 488, 489, 492, 513, 516, 527, 529, 547, 574, 614, 617, 712, 724 and 742.

2. An isolated human signal transducer and activator of transcription 4 (hStat 4) protein or fragment thereof according to claim 1, wherein the fragment of SEQ ID NO:2 comprises residue 40.

3. An isolated human signal transducer and activator of transcription 4 (hStat 4) protein or fragment thereof according to claim 1, wherein the fragment of SEQ ID NO:2 comprises residue 45.

4. An isolated human signal transducer and activator of transcription 4 (hStat 4) protein or fragment thereof according to claim 1, wherein the fragment of SEQ ID NO:2 comprises residue 123.

5. An isolated human signal transducer and activator of transcription 4 (hStat 4) protein or fragment thereof according to claim 1, wherein the fragment of SEQ ID NO:2 comprises residue 148.

6. An isolated human signal transducer and activator of transcription 4 (hStat 4) protein or fragment thereof according to claim 1, wherein the fragment of SEQ ID NO:2 comprises residue 184.

7. An isolated human signal transducer and activator of transcription 4 (hStat 4) protein or fragment thereof according to claim 1, wherein the fragment of SEQ ID NO:2 comprises residue 189.

8. An isolated human signal transducer and activator of transcription 4 (hStat 4) protein or fragment thereof according to claim 1, wherein the fragment of SEQ ID NO:2 comprises residue 190.

9. An isolated human signal transducer and activator of transcription 4 (hStat 4) protein or fragment thereof according to claim 1, wherein the fragment of SEQ ID NO:2 comprises residue 220.

10. An isolated human signal transducer and activator of transcription 4 (hStat 4) protein or fragment thereof according to claim 1, wherein the fragment of SEQ ID NO:2 comprises residue 221.

11. An isolated human signal transducer and activator of transcription 4 (hStat 4) protein or fragment thereof according to claim 1, wherein the fragment of SEQ ID NO:2 comprises residue 229.

12. An isolated human signal transducer and activator of transcription 4 (hStat 4) protein or fragment thereof according to claim 1, wherein the fragment of SEQ ID NO:2 comprises residue 232.

13. An isolated human signal transducer and activator of transcription 4 (hStat 4) protein or fragment thereof according to claim 1, wherein the fragment of SEQ ID NO:2 comprises residue 240.

14. An isolated human signal transducer and activator of transcription 4 (hStat 4) protein or fragment thereof according to claim 1, wherein the fragment of SEQ ID NO:2 comprises residue 274.

15. An isolated human signal transducer and activator of transcription 4 (hStat 4) protein or fragment thereof according to claim 1, wherein the fragment of SEQ ID NO:2 comprises residue 280.

16. An isolated human signal transducer and activator of transcription 4 (hStat 4) protein or fragment thereof according to claim 1, wherein the fragment of SEQ ID NO:2 comprises residue 295.

17. An isolated human signal transducer and activator of transcription 4 (hStat 4) protein or fragment thereof according to claim 1, wherein the fragment of SEQ ID NO:2 comprises residue 298.

18. An isolated human signal transducer and activator of transcription 4 (hStat 4) protein or fragment thereof according to claim 1, wherein the fragment of SEQ ID NO:2 comprises residue 300.

19. An isolated human signal transducer and activator of transcription 4 (hStat 4) protein or fragment thereof according to claim 1, wherein the fragment of SEQ ID NO:2 comprises residue 304.

20. An isolated human signal transducer and activator of transcription 4 (hStat 4) protein or fragment thereof according to claim 1, wherein the fragment of SEQ ID NO:2 comprises residue 332.

21. An isolated human signal transducer and activator of transcription 4 (hStat 4) protein or fragment thereof according to claim 1, wherein the fragment of SEQ ID NO:2 comprises residue 381.

22. An isolated human signal transducer and activator of transcription 4 (hStat 4) protein or fragment thereof according to claim 1, wherein the fragment of SEQ ID NO:2 comprises residue 387.

23. An isolated human signal transducer and activator of transcription 4 (hStat 4) protein or fragment thereof according to claim 1, wherein the fragment of SEQ ID NO:2 comprises residue 409.

24. An isolated human signal transducer and activator of transcription 4 (hStat 4) protein or fragment thereof according to claim 1, wherein the fragment of SEQ ID NO:2 comprises residue 411.

25. An isolated human signal transducer and activator of transcription 4 (hStat 4) protein or fragment thereof according to claim 1, wherein the fragment of SEQ ID NO:2 comprises residue 413.

26. An isolated human signal transducer and activator of transcription 4 (hStat 4) protein or fragment thereof according to claim 1, wherein the fragment of SEQ ID NO:2 comprises residue 443.

27. An isolated human signal transducer and activator of transcription 4 (hStat 4) protein or fragment thereof according to claim 1, wherein the fragment of SEQ ID NO:2 comprises residue 488.

28. An isolated human signal transducer and activator of transcription 4 (hStat 4) protein or fragment thereof according to claim 1, wherein the fragment of SEQ ID NO:2 comprises residue 489.

29. An isolated human signal transducer and activator of transcription 4 (hStat 4) protein or fragment thereof according to claim 1, wherein the fragment of SEQ ID NO:2 comprises residue 492.

30. An isolated human signal transducer and activator of transcription 4 (hStat 4) protein or fragment thereof according to claim 1, wherein the fragment of SEQ ID NO:2 comprises residue 513.

31. An isolated human signal transducer and activator of transcription 4 (hStat 4) protein or fragment thereof according to claim 1, wherein the fragment of SEQ ID NO:2 comprises residue 516.

32. An isolated human signal transducer and activator of transcription 4 (hStat 4) protein or fragment thereof according to claim 1, wherein the fragment of SEQ ID NO:2 comprises residue 527.

33. An isolated human signal transducer and activator of transcription 4 (hStat 4) protein or fragment thereof according to claim 1, wherein the fragment of SEQ ID NO:2 comprises residue 529.

34. An isolated human signal transducer and activator of transcription 4 (hStat 4) protein or fragment thereof according to claim 1, wherein the fragment of SEQ ID NO:2 comprises residue 547.

35. An isolated human signal transducer and activator of transcription 4 (hStat 4) protein or fragment thereof according to claim 1, wherein the fragment of SEQ ID NO:2 comprises residue 574.

36. An isolated human signal transducer and activator of transcription 4 (hStat 4) protein or fragment thereof according to claim 1, wherein the fragment of SEQ ID NO:2 comprises residue 614.

37. An isolated human signal transducer and activator of transcription 4 (hStat 4) protein or fragment thereof according to claim 1, wherein the fragment of SEQ ID NO:2 comprises residue 617.

38. An isolated human signal transducer and activator of transcription 4 (hStat 4) protein or fragment thereof according to claim 1, wherein the fragment of SEQ ID NO:2 comprises residue 712.

39. An isolated human signal transducer and activator of transcription 4 (hStat 4) protein or fragment thereof according to claim 1, wherein the fragment of SEQ ID NO:2 comprises residue 724.

40. An isolated human signal transducer and activator of transcription 4 (hStat 4) protein or fragment thereof according to claim 1, wherein the fragment of SEQ ID NO:2 comprises residue 742.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 2606 base pairs
( B ) TYPE: nucleic acid
( C ) STRANDEDNESS: single
( D ) TOPOLOGY: linear ( i i ) MOLECULE TYPE: cDNA 5,639,858

( i x ) FEATURE:
    ( A ) NAME/KEY: CDS
    ( B ) LOCATION: 82..2324

( i x ) FEATURE:
    ( A ) NAME/KEY: CDS
    ( B ) LOCATION: 82..2328

( x i ) SEQUENCE DESCRIPTION: SEQ ID NO:1:

```
GCTTTCTCCT AGGGACTGTG AGGGGCGCTT CTGACTTTGG ACTTGAGCAC TGCCTGGGAC                    60

CTGTGCTGAG AGAGCGCTAG C ATG TCT CAG TGG AAT CAA GTC CAA CAG TTA                    111
                        Met Ser Gln Trp Asn Gln Val Gln Gln Leu
                         1           5                      10

GAA ATC AAG TTT TTG GAG CAG GTG GAT CAA TTC TAT GAT GAC AAC TTT                    159
Glu Ile Lys Phe Leu Glu Gln Val Asp Gln Phe Tyr Asp Asp Asn Phe
             15                  20                  25

CCC ATG GAA ATT CGG CAT CTG TTG GCC CAA TGG ATT GAA AAT CAA GAC                    207
Pro Met Glu Ile Arg His Leu Leu Ala Gln Trp Ile Glu Asn Gln Asp
         30                  35                  40

TGG GAG GCA GCT TCT AAC AAT GAA ACC ATG GCA ACG ATT CTT CTT CAA                    255
Trp Glu Ala Ala Ser Asn Asn Glu Thr Met Ala Thr Ile Leu Leu Gln
     45                  50                  55

AAC TTG TTA ATA CAA CTG GAT GAA CAG TTA GGT CGT GTT TCC AAA GAG                    303
Asn Leu Leu Ile Gln Leu Asp Glu Gln Leu Gly Arg Val Ser Lys Glu
 60                  65                  70

AAA AAC CTA CTC TTG ATA CAC AAT CTA AAA AGA ATT AGG AAG GTC CTT                    351
Lys Asn Leu Leu Leu Ile His Asn Leu Lys Arg Ile Arg Lys Val Leu
 75                  80                  85                  90

CAG GGA AAA TTT CAT GGA AAT CCA ATG CAT GTA GCT GTG GTT ATT TCA                    399
Gln Gly Lys Phe His Gly Asn Pro Met His Val Ala Val Val Ile Ser
                 95                 100                 105

AAC TGT TTA AGG GAA GAG AGG AGA ATA TTG GCT GCA GCC AAC ATG CCT                    447
Asn Cys Leu Arg Glu Glu Arg Arg Ile Leu Ala Ala Ala Asn Met Pro
             110                 115                 120

GTC CAG GGG CCT CTA GAG AAA TCC TTA CAA AGT TCT TCA GTT TCA GAA                    495
Val Gln Gly Pro Leu Glu Lys Ser Leu Gln Ser Ser Ser Val Ser Glu
         125                 130                 135

AGA CAG AGG AAT GTG GAG CAC AAA GTG GCT GCC ATT AAA AAC AGT GTG                    543
Arg Gln Arg Asn Val Glu His Lys Val Ala Ala Ile Lys Asn Ser Val
     140                 145                 150

CAG ATG ACA GAA CAA GAT ACC AAA TAC TTA GAA GAT CTG CAA GAC GAA                    591
Gln Met Thr Glu Gln Asp Thr Lys Tyr Leu Glu Asp Leu Gln Asp Glu
155                 160                 165                 170

TTT GAC TAC AGG TAT AAA ACA ATT CAG ACA ATG GAT CAG AGT GAC AAG                    639
Phe Asp Tyr Arg Tyr Lys Thr Ile Gln Thr Met Asp Gln Ser Asp Lys
                 175                 180                 185

AAT AGT GCC ATG GTG AAT CAG GAA GTT TTG ACA CTG CAG GAA ATG CTT                    687
Asn Ser Ala Met Val Asn Gln Glu Val Leu Thr Leu Gln Glu Met Leu
             190                 195                 200

AAC AGC CTC GAT TTC AAG AGA AAG GAG GCT CTC AGT AAA ATG ACC CAA                    735
Asn Ser Leu Asp Phe Lys Arg Lys Glu Ala Leu Ser Lys Met Thr Gln
         205                 210                 215

ATC ATC CAT GAG ACA GAC CTG TTA ATG AAC ACC ATG CTC ATA GAA GAG                    783
Ile Ile His Glu Thr Asp Leu Leu Met Asn Thr Met Leu Ile Glu Glu
 220                 225                 230

CTG CAA GAC TGG AAG CGG CGG CAG CAA ATC GCC TGC ATC GGG GGT CCA                    831
Leu Gln Asp Trp Lys Arg Arg Gln Gln Ile Ala Cys Ile Gly Gly Pro
235                 240                 245                 250

CTC CAC AAT GGG CTC GAC CAG CTT CAG AAC TGC TTT ACA CTA TTG GCA                    879
Leu His Asn Gly Leu Asp Gln Leu Gln Asn Cys Phe Thr Leu Leu Ala
                 255                 260                 265
```

```
GAA AGT CTT TTC CAA CTG AGA AGG CAA TTG GAG AAA CTA GAG GAG CAA        927
Glu Ser Leu Phe Gln Leu Arg Arg Gln Leu Glu Lys Leu Glu Glu Gln
        270             275             280

TCT ACC AAA ATG ACA TAT GAA GGT GAT CCC ATT CCA ATG CAA AGA ACT        975
Ser Thr Lys Met Thr Tyr Glu Gly Asp Pro Ile Pro Met Gln Arg Thr
        285             290             295

CAC ATG CTA GAA AGA GTC ACC TTC TTG ATC TAC AAC CTT TTC AAG AAC       1023
His Met Leu Glu Arg Val Thr Phe Leu Ile Tyr Asn Leu Phe Lys Asn
        300             305             310

TCA TTT GTG GTT GAG CGA CAG CCA TGT ATG CCA ACC CAC CCT CAG AGG       1071
Ser Phe Val Val Glu Arg Gln Pro Cys Met Pro Thr His Pro Gln Arg
315         320             325             330

CCG TTG GTA CTT AAA ACC CTA ATT CAG TTC ACT GTA AAA CTA AGG CTA       1119
Pro Leu Val Leu Lys Thr Leu Ile Gln Phe Thr Val Lys Leu Arg Leu
                335             340             345

CTA ATA AAA TTG CCA GAA CTA AAC TAT CAG GTA AAG GTT AAG GCA TCA       1167
Leu Ile Lys Leu Pro Glu Leu Asn Tyr Gln Val Lys Val Lys Ala Ser
            350             355             360

ATT GAC AAG AAT GTT TCA ACT CTA AGC AAC CGA AGA TTT GTA CTT TGT       1215
Ile Asp Lys Asn Val Ser Thr Leu Ser Asn Arg Arg Phe Val Leu Cys
        365             370             375

GGA ACT AAT GTC AAA GCC ATG TCT ATT GAA GAA TCT TCC AAT GGG AGT       1263
Gly Thr Asn Val Lys Ala Met Ser Ile Glu Glu Ser Ser Asn Gly Ser
        380             385             390

CTC TCA GTA GAA TTT CGA CAT TTG CAA CCA AAG GAA ATG AAG TCC AGT       1311
Leu Ser Val Glu Phe Arg His Leu Gln Pro Lys Glu Met Lys Ser Ser
395         400             405             410

GCT GGA GGT AAA GGA AAT GAG GGC TGT CAC ATG GTG ACT GAA GAA CTT       1359
Ala Gly Gly Lys Gly Asn Glu Gly Cys His Met Val Thr Glu Glu Leu
            415             420             425

CAT TCC ATA ACG TTT GAA ACA CAG ATC TGC CTC TAT GGC CTG ACC ATA       1407
His Ser Ile Thr Phe Glu Thr Gln Ile Cys Leu Tyr Gly Leu Thr Ile
        430             435             440

GAT TTG GAG ACC AGC TCA TTG CCT GTG GTG ATG ATT TCC AAT GTC AGT       1455
Asp Leu Glu Thr Ser Ser Leu Pro Val Val Met Ile Ser Asn Val Ser
        445             450             455

CAG TTA CCT AAT GCT TGG GCA TCC ATC ATT TGG TAC AAC GTG TCA ACC       1503
Gln Leu Pro Asn Ala Trp Ala Ser Ile Ile Trp Tyr Asn Val Ser Thr
        460             465             470

AAC GAT TCC CAG AAC TTG GTT TTC TTT AAT AAT CCT CCA CCT GCC ACA       1551
Asn Asp Ser Gln Asn Leu Val Phe Phe Asn Asn Pro Pro Pro Ala Thr
475         480             485             490

TTG AGT CAA CTA CTG GAG GTG ATG AGC TGG CAG TTT TCA TCG TAC GTT       1599
Leu Ser Gln Leu Leu Glu Val Met Ser Trp Gln Phe Ser Ser Tyr Val
            495             500             505

GGT CGT GGT CTT AAC TCA GAT CAA CTC CAT ATG CTG GCA GAG AAG CTT       1647
Gly Arg Gly Leu Asn Ser Asp Gln Leu His Met Leu Ala Glu Lys Leu
        510             515             520

ACA GTC CAA TCT AGC TAC AGT GAT GGT CAC CTC ACC TGG GCC AAG TTC       1695
Thr Val Gln Ser Ser Tyr Ser Asp Gly His Leu Thr Trp Ala Lys Phe
        525             530             535

TGC AAG GAA CAT TTA CCT GGT AAA TCA TTT ACC TTT TGG ACA TGG CTT       1743
Cys Lys Glu His Leu Pro Gly Lys Ser Phe Thr Phe Trp Thr Trp Leu
540             545             550

GAA GCA ATA TTG GAT CTA ATT AAG AAA CAC ATT CTT CCC CTT TGG ATT       1791
Glu Ala Ile Leu Asp Leu Ile Lys Lys His Ile Leu Pro Leu Trp Ile
555             560             565             570

GAT GGG TAT GTC ATG GGC TTT GTT AGC AAA GAG AAG GAA CGG CTG TTG       1839
Asp Gly Tyr Val Met Gly Phe Val Ser Lys Glu Lys Glu Arg Leu Leu
            575             580             585
```

| | | | | | | | | | | | | | | | | |
|---|---|---|---|---|---|---|---|---|---|---|---|---|---|---|---|---|
| CTA | AAG | GAT | AAA | ATG | CCT | GGC | ACC | TTT | TTA | TTA | AGA | TTC | AGT | GAA | AGC | 1887 |
| Leu | Lys | Asp | Lys | Met | Pro | Gly | Thr | Phe | Leu | Leu | Arg | Phe | Ser | Glu | Ser | |
| | | | 590 | | | | 595 | | | | | | 600 | | | |
| CAT | CTC | GGA | GGA | ATA | ACT | TTC | ACC | TGG | GTG | GAC | CAT | TCT | GAA | AGT | GGG | 1935 |
| His | Leu | Gly | Gly | Ile | Thr | Phe | Thr | Trp | Val | Asp | His | Ser | Glu | Ser | Gly | |
| | | 605 | | | | | 610 | | | | | 615 | | | | |
| GAA | GTG | AGA | TTC | CAC | TCT | GTA | GAA | CCC | TAC | AAT | AAA | GGC | CGG | TTG | TCT | 1983 |
| Glu | Val | Arg | Phe | His | Ser | Val | Glu | Pro | Tyr | Asn | Lys | Gly | Arg | Leu | Ser | |
| | 620 | | | | | 625 | | | | | 630 | | | | | |
| GCT | CTG | CCA | TTC | GCT | GAC | ATC | CTG | CGA | GAC | TAC | AAA | GTT | ATT | ATG | GCT | 2031 |
| Ala | Leu | Pro | Phe | Ala | Asp | Ile | Leu | Arg | Asp | Tyr | Lys | Val | Ile | Met | Ala | |
| 635 | | | | 640 | | | | | 645 | | | | | | 650 | |
| GAA | AAC | ATT | CCT | GAA | AAC | CCT | CTG | AAG | TAC | CTA | TAT | CCT | GAC | ATT | CCC | 2079 |
| Glu | Asn | Ile | Pro | Glu | Asn | Pro | Leu | Lys | Tyr | Leu | Tyr | Pro | Asp | Ile | Pro | |
| | | | | 655 | | | | | 660 | | | | | 665 | | |
| AAA | GAC | AAA | GCC | TTC | GGT | AAA | CAC | TAC | AGC | TCT | CAG | CCT | TGC | GAA | GTT | 2127 |
| Lys | Asp | Lys | Ala | Phe | Gly | Lys | His | Tyr | Ser | Ser | Gln | Pro | Cys | Glu | Val | |
| | | | 670 | | | | | 675 | | | | | 680 | | | |
| TCA | AGA | CCA | ACA | GAA | AGG | GGT | GAC | AAA | GGT | TAT | GTT | CCT | TCT | GTT | TTT | 2175 |
| Ser | Arg | Pro | Thr | Glu | Arg | Gly | Asp | Lys | Gly | Tyr | Val | Pro | Ser | Val | Phe | |
| | | 685 | | | | | 690 | | | | | 695 | | | | |
| ATC | CCC | ATC | TCA | ACA | ATC | CGA | AGT | GAT | TCA | ACA | GAG | CCA | CAT | TCT | CCA | 2223 |
| Ile | Pro | Ile | Ser | Thr | Ile | Arg | Ser | Asp | Ser | Thr | Glu | Pro | His | Ser | Pro | |
| | 700 | | | | | 705 | | | | | 710 | | | | | |
| TCA | GAC | CTT | CTT | CCC | ATG | TCT | CCA | AGT | GTG | TAT | GCG | GTG | TTG | AGA | GAA | 2271 |
| Ser | Asp | Leu | Leu | Pro | Met | Ser | Pro | Ser | Val | Tyr | Ala | Val | Leu | Arg | Glu | |
| 715 | | | | | 720 | | | | | 725 | | | | | 730 | |
| AAC | CTG | AGT | CCC | ACA | ACA | ATT | GAA | ACT | GCA | ATG | AAG | TCT | CCT | TAT | TCT | 2319 |
| Asn | Leu | Ser | Pro | Thr | Thr | Ile | Glu | Thr | Ala | Met | Lys | Ser | Pro | Tyr | Ser | |
| | | | | 735 | | | | | 740 | | | | | 745 | | |
| GCT | GAA | TGA | CAGGATAAAC | TCTGACGCAC | CAAGAAAGGA | AGCAAATGAA | | | | | | | | | | 2368 |
| Ala | Glu | * | | | | | | | | | | | | | | |
| AAAGTTTAAA | GACTGTTCTT | TGCCCAATAA | CCACATTTTA | TTTCTTCAGC | TTTGTAAATA | | | | | | | | | | | 2428 |
| CCAGGTTCTA | GGAAATGTTT | GACATCTGAA | GCTCTCTTCA | CACTCCCGTG | GCACTCCTCA | | | | | | | | | | | 2488 |
| ATTGGGAGTG | TTGTGACTGA | AATGCTTGAA | ACCAAAGCTT | CAGATAAACT | TGCAAGATAA | | | | | | | | | | | 2548 |
| GACAACTTTA | AGAAACCAGT | GTTAATAACA | ATATTAACAG | AAAAAAAAA | AAAAAAA | | | | | | | | | | | 2606 |

( 2 ) INFORMATION FOR SEQ ID NO:2:

( i ) SEQUENCE CHARACTERISTICS:
  ( A ) LENGTH: 748 amino acids
  ( B ) TYPE: amino acid
  ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ser | Gln | Trp | Asn | Gln | Val | Gln | Gln | Leu | Glu | Ile | Lys | Phe | Leu | Glu |
| 1 | | | | 5 | | | | | 10 | | | | | 15 | |
| Gln | Val | Asp | Gln | Phe | Tyr | Asp | Asp | Asn | Phe | Pro | Met | Glu | Ile | Arg | His |
| | | | 20 | | | | | 25 | | | | | 30 | | |
| Leu | Leu | Ala | Gln | Trp | Ile | Glu | Asn | Gln | Asp | Trp | Glu | Ala | Ala | Ser | Asn |
| | | | 35 | | | | 40 | | | | | 45 | | | |
| Asn | Glu | Thr | Met | Ala | Thr | Ile | Leu | Leu | Gln | Asn | Leu | Leu | Ile | Gln | Leu |
| | | 50 | | | | | 55 | | | | | 60 | | | |
| Asp | Glu | Gln | Leu | Gly | Arg | Val | Ser | Lys | Glu | Lys | Asn | Leu | Leu | Leu | Ile |
| 65 | | | | | 70 | | | | | 75 | | | | | 80 |
| His | Asn | Leu | Lys | Arg | Ile | Arg | Lys | Val | Leu | Gln | Gly | Lys | Phe | His | Gly |
| | | | | 85 | | | | | 90 | | | | | 95 | |

```
Asn  Pro  Met  His  Val  Ala  Val  Val  Ile  Ser  Asn  Cys  Leu  Arg  Glu  Glu
               100                      105                      110

Arg  Arg  Ile  Leu  Ala  Ala  Ala  Asn  Met  Pro  Val  Gln  Gly  Pro  Leu  Glu
          115                      120                      125

Lys  Ser  Leu  Gln  Ser  Ser  Ser  Val  Ser  Glu  Arg  Gln  Arg  Asn  Val  Glu
     130                      135                      140

His  Lys  Val  Ala  Ala  Ile  Lys  Asn  Ser  Val  Gln  Met  Thr  Glu  Gln  Asp
145                           150                      155                 160

Thr  Lys  Tyr  Leu  Glu  Asp  Leu  Gln  Asp  Glu  Phe  Asp  Tyr  Arg  Tyr  Lys
                    165                      170                      175

Thr  Ile  Gln  Thr  Met  Asp  Gln  Ser  Asp  Lys  Asn  Ser  Ala  Met  Val  Asn
               180                      185                      190

Gln  Glu  Val  Leu  Thr  Leu  Gln  Glu  Met  Leu  Asn  Ser  Leu  Asp  Phe  Lys
          195                      200                      205

Arg  Lys  Glu  Ala  Leu  Ser  Lys  Met  Thr  Gln  Ile  Ile  His  Glu  Thr  Asp
     210                      215                      220

Leu  Leu  Met  Asn  Thr  Met  Leu  Ile  Glu  Glu  Leu  Gln  Asp  Trp  Lys  Arg
225                      230                      235                      240

Arg  Gln  Gln  Ile  Ala  Cys  Ile  Gly  Gly  Pro  Leu  His  Asn  Gly  Leu  Asp
               245                      250                      255

Gln  Leu  Gln  Asn  Cys  Phe  Thr  Leu  Leu  Ala  Glu  Ser  Leu  Phe  Gln  Leu
               260                      265                      270

Arg  Arg  Gln  Leu  Glu  Lys  Leu  Glu  Glu  Gln  Ser  Thr  Lys  Met  Thr  Tyr
          275                      280                      285

Glu  Gly  Asp  Pro  Ile  Pro  Met  Gln  Arg  Thr  His  Met  Leu  Glu  Arg  Val
     290                      295                      300

Thr  Phe  Leu  Ile  Tyr  Asn  Leu  Phe  Lys  Asn  Ser  Phe  Val  Val  Glu  Arg
305                      310                      315                      320

Gln  Pro  Cys  Met  Pro  Thr  His  Pro  Gln  Arg  Pro  Leu  Val  Leu  Lys  Thr
               325                      330                      335

Leu  Ile  Gln  Phe  Thr  Val  Lys  Leu  Arg  Leu  Leu  Ile  Lys  Leu  Pro  Glu
               340                      345                      350

Leu  Asn  Tyr  Gln  Val  Lys  Val  Lys  Ala  Ser  Ile  Asp  Lys  Asn  Val  Ser
          355                      360                      365

Thr  Leu  Ser  Asn  Arg  Arg  Phe  Val  Leu  Cys  Gly  Thr  Asn  Val  Lys  Ala
     370                      375                      380

Met  Ser  Ile  Glu  Glu  Ser  Ser  Asn  Gly  Ser  Leu  Ser  Val  Glu  Phe  Arg
385                      390                      395                      400

His  Leu  Gln  Pro  Lys  Glu  Met  Lys  Ser  Ser  Ala  Gly  Gly  Lys  Gly  Asn
               405                      410                      415

Glu  Gly  Cys  His  Met  Val  Thr  Glu  Glu  Leu  His  Ser  Ile  Thr  Phe  Glu
               420                      425                      430

Thr  Gln  Ile  Cys  Leu  Tyr  Gly  Leu  Thr  Ile  Asp  Leu  Glu  Thr  Ser  Ser
               435                      440                      445

Leu  Pro  Val  Val  Met  Ile  Ser  Asn  Val  Ser  Gln  Leu  Pro  Asn  Ala  Trp
     450                      455                      460

Ala  Ser  Ile  Ile  Trp  Tyr  Asn  Val  Ser  Thr  Asn  Asp  Ser  Gln  Asn  Leu
465                      470                      475                      480

Val  Phe  Phe  Asn  Asn  Pro  Pro  Ala  Thr  Leu  Ser  Gln  Leu  Leu  Glu
                    485                      490                      495

Val  Met  Ser  Trp  Gln  Phe  Ser  Ser  Tyr  Val  Gly  Arg  Gly  Leu  Asn  Ser
               500                      505                      510
```

| | | | | | | | | | | | | | | |
|---|---|---|---|---|---|---|---|---|---|---|---|---|---|---|
| Asp | Gln | Leu 515 | His | Met | Leu | Ala | Glu 520 | Lys | Leu | Thr | Val | Gln 525 | Ser | Ser | Tyr |
| Ser | Asp 530 | Gly | His | Leu | Thr | Trp 535 | Ala | Lys | Phe | Cys | Lys 540 | Glu | His | Leu | Pro |
| Gly 545 | Lys | Ser | Phe | Thr | Phe 550 | Trp | Thr | Trp | Leu | Glu 555 | Ala | Ile | Leu | Asp | Leu 560 |
| Ile | Lys | Lys | His | Ile 565 | Leu | Pro | Leu | Trp | Ile 570 | Asp | Gly | Tyr | Val | Met 575 | Gly |
| Phe | Val | Ser | Lys 580 | Glu | Lys | Glu | Arg | Leu 585 | Leu | Leu | Lys | Asp | Lys 590 | Met | Pro |
| Gly | Thr | Phe 595 | Leu | Leu | Arg | Phe | Ser 600 | Glu | Ser | His | Leu | Gly 605 | Gly | Ile | Thr |
| Phe | Thr 610 | Trp | Val | Asp | His | Ser 615 | Glu | Ser | Gly | Glu | Val 620 | Arg | Phe | His | Ser |
| Val 625 | Glu | Pro | Tyr | Asn | Lys 630 | Gly | Arg | Leu | Ser | Ala 635 | Leu | Pro | Phe | Ala | Asp 640 |
| Ile | Leu | Arg | Asp | Tyr 645 | Lys | Val | Ile | Met | Ala 650 | Glu | Asn | Ile | Pro | Glu 655 | Asn |
| Pro | Leu | Lys | Tyr 660 | Leu | Tyr | Pro | Asp | Ile 665 | Pro | Lys | Asp | Lys | Ala 670 | Phe | Gly |
| Lys | His | Tyr 675 | Ser | Ser | Gln | Pro | Cys 680 | Glu | Val | Ser | Arg | Pro 685 | Thr | Glu | Arg |
| Gly | Asp 690 | Lys | Gly | Tyr | Val | Pro 695 | Ser | Val | Phe | Ile | Pro 700 | Ile | Ser | Thr | Ile |
| Arg 705 | Ser | Asp | Ser | Thr | Glu 710 | Pro | His | Ser | Pro | Ser 715 | Asp | Leu | Leu | Pro | Met 720 |
| Ser | Pro | Ser | Val | Tyr 725 | Ala | Val | Leu | Arg | Glu 730 | Asn | Leu | Ser | Pro | Thr 735 | Thr |
| Ile | Glu | Thr | Ala 740 | Met | Lys | Ser | Pro | Tyr 745 | Ser | Ala | Glu |

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GTATTTCCCA GAAAAGGAAC          20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GTATCACCCA GTCAAGGAAC          20